(12) United States Patent
Woods et al.

(10) Patent No.: US 7,717,940 B2
(45) Date of Patent: May 18, 2010

(54) CROSS-CONNECTOR ASSEMBLY

(75) Inventors: Richard W. Woods, Catonsville, MD (US); Christopher B. Straight, Leesburg, VA (US); Todd M. Wallenstein, Ashburn, VA (US)

(73) Assignee: K2M, Inc., Leesburg, VA (US)

( * ) Notice: Subject to any disclaimer, the term of this patent is extended or adjusted under 35 U.S.C. 154(b) by 777 days.

(21) Appl. No.: 11/437,631

(22) Filed: May 22, 2006

(65) Prior Publication Data

US 2007/0016197 A1    Jan. 18, 2007

(51) Int. Cl.
*A61B 17/70* (2006.01)
(52) U.S. Cl. .................. 606/253; 606/250; 606/252; 606/278
(58) Field of Classification Search .............. 606/60, 606/61, 64, 250, 278, 251, 252, 253; 403/87, 403/90, 110, 177, 196, 362, 382
See application file for complete search history.

(56) References Cited

U.S. PATENT DOCUMENTS

| | | | |
|---|---|---|---|
| 6,554,832 B2 * | 4/2003 | Shluzas | 606/252 |
| 6,602,253 B2 * | 8/2003 | Richelsoph et al. | 606/252 |
| 6,602,291 B1 | 8/2003 | Ray et al. | |
| 6,887,241 B1 | 5/2005 | McBride et al. | |
| 7,104,992 B2 * | 9/2006 | Bailey | 606/278 |
| 2004/0133203 A1 * | 7/2004 | Young et al. | 606/61 |
| 2006/0229607 A1 * | 10/2006 | Brumfield | 606/61 |

OTHER PUBLICATIONS

International Search Report issued in International Application No. PCT/US06/19770 on Nov. 27, 2006 (2 pages).

* cited by examiner

*Primary Examiner*—Eduardo C Robert
*Assistant Examiner*—Lynnsy Schneider
(74) *Attorney, Agent, or Firm*—Perry E. Van Over & Associates PLLC

(57) ABSTRACT

A novel cross-connector assembly for interconnecting first and second bracing members or rods, one to the other. The cross-connector assembly is capable of multi-directional articulation in three dimensions, length, azimuth, and elevation and is also capable of having one end rotated along its longitudinal axis in relation to the other end so as to custom fit and securely connect the assembly to two opposing bracing members or rods. Also provided is a kit including the device and ancillary instrumentation to facilitate the method of the present invention.

10 Claims, 4 Drawing Sheets

CROSS-CONNECTOR ASSEMBLY

BACKGROUND OF THE INVENTION

1. Field of the Invention

The present invention relates to a novel cross-connector assembly for interconnecting a first and a second bracing member or rod, which are in relative opposition to each other. More particularly the present invention relates to a novel multi-directional articulating cross-connector assembly configured to be simultaneously articulated in four directions including to be rotated in-part so as to custom fit to and securely connect two relatively parallel-aligned spinal rods, which are positioned along the longitudinal axis of a subject's spinal column.

2. Background of the Technology

Spinal fixation apparatuses are widely employed in surgical processes for correcting spinal injuries and diseases. These apparatuses commonly employ longitudinal link rods secured to coupling elements and are secured to the bone such as vertebrae by spinal bone fixation fasteners such as pedicle screws, hooks and others. The opposing pair of longitudinal link rods are commonly disposed along the longitudinal axis of the spine and are held in position relative to one another by cross-connectors, also known as transverse connectors or transverse bridge elements.

As the technology of spinal surgery has developed and improved, each of the necessary spinal fixation components has also undergone improvements and modifications to address the short-comings of conventional spinal appliances. While some improvements have been made in the design and operation of cross-connectors for spinal rods, there remains an unfulfilled need for a cross-connector that provides simplicity of operation with a minimal number of parts, which can provide reliable, secure attachment of two spinal rods that due to the natural and variable contours of the subject's spine are seldom in a perfectly parallel disposition, one to the other.

To meet the problem of securely connecting two opposing spinal rods together, a requirement exists to provide a cross-connector that can easily be manipulated during surgery in four directions to include being rotated in-part about the longitudinal axis of the connector; that is, a device is required that can rotate around each of the three axis of the device and also be translated to shorten or lengthen the device along its longitudinal axis before being securely locked into the desired position. In addition, the connector should be configured to provide a low profile with the smoothest possible contoured external surfaces to avoid irritation of adjacent soft tissue and thus promote healing and comfort for the subject post surgery.

Conventional efforts to meet this need have fallen short of the desired cross-connector configuration. For example, U.S. Pat. No. 6,554,832, issued to Shluzas, as best seen in FIGS. 2 and 4 of that patent, provides a transverse connector, which includes first and second connector members for connection to the respective first and second spine rods. The two connector members are connected one to the other by a connecting rod, which can be withdrawn or extended in alignment with the longitudinal axis of the cross-connector for purpose of adjusting the length thereof. As shown in FIG. 2 of the Shluzas patent, the extent of movement of the connecting rod (Shluzas at 42) inwardly through the opening (40) is limited by the design of the device, which after allowing a limited amount of inward movement of the connecting rod will impede further inward movement when the connecting rod (Shluzas at 42) comes into contact with the inwardly disposed portion of the connecting member (Shluzas at 30), the spine rod (Shluzas at 12), or possibly the set screw (Shluzas at 34). The design of the Shluzas connector thus provides a very limited inward adjustment of the length of the device. The device of Shluzas is also configured such that the connecting rod can be pivoted about a pivot axis to adjust the azimuth of the axis of the first connector in relation to the axis of the second connector. That is, the Shluzas device allows the surgeon to pivot the connecting rod about a pivot axis thus allowing one end of the multi-part transverse connector to be pivotally adjusted away from the longitudinal axis of the other end of the connector either caudally or cephallicly in relation to the subject's spinal column. Importantly the pivoting movement of the Shluzas connector is limited to movement within the same horizontal plane relative to the longitudinal axis of the spinal cord. Thus, while the device of Shluzas does permit some limited adjustment in length and azimuth of the device, it is configured to structurally prohibit any upward or downward movement in relation to the surface plane of the spinal column. That is, the elevation of one end of the Shluzas connector relative to the other end of the connector cannot be adjusted. While the connector of Shluzas does provide some improvement over earlier such devices, it still falls short of the need to provide a connector that can simultaneously be configured to be rotationally adjustable about each of the three axis and translated along the length of its longitudinal axis. That is, the device of Shluzas cannot be adjusted in all three planes: length, azimuth, and elevation as well as be rotated in-part around the connector's longitudinal axis.

Thus a need exists for a cross-connector assembly that provides ease of operation by the surgeon to adjust one connecting end of the assembly in relation to the other end of the assembly by rotation of the device around each of the three axis and translated in length along the longitudinal axis, to securely lock the assembly in the selected configuration, and to provide a cross-connector that has a low profile and the smoothest possible external surface contours to promote healing and minimal irritation of adjacent soft tissues in the subject.

SUMMARY OF THE INVENTION

The cross-connector assembly and method of application of the present invention provides a novel multi-directional articulating cross-connector assembly configured to be capable of being simultaneously articulated in the three dimensions of length, azimuth, and elevation and to be rotated about its longitudinal axis so as to custom fit to and securely connect two opposing rods or bracing members, which are positioned in opposition to each other along the bone portions being secured by the assembly.

Also provided is a novel articulation member as part of an articulating and locking component of the multi-directional cross-connector assembly, that articulation member enabling multi-directional manipulation of the assembly and also providing a secure locking function to maintain the assembly in the selected configuration.

Also provided is a novel cross-connector assembly, which can be securely locked into a selected position relative to the two opposing rods or bracing members, the locking members being configured to provide a low profile and a smooth external surface contour to avoid irritation of adjacent soft tissue and thus promote healing.

Also provided is a kit that can include at least one of the novel cross-connection assemblies of the present invention, a set of securing members or screws adapted for attaching spinal rods to the bone of a subject, a set of spinal rods, and surgical instruments configured to be capable of facilitating the insertion of the cross-connector assembly into a subject and the fixation of the device to the spinal rods.

Also provided is a method of using the novel cross-connector assembly of the present invention such that the surgical procedure employed, in comparison to conventional methods, is quickly accomplished with low risk to the subject to which the assembly is being surgically attached.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein.

DETAILED DESCRIPTION OF THE INVENTION

Detailed embodiments of the present invention are disclosed herein; however, it is understood that the following description is provided as being exemplary of the invention, which may be embodied in various forms without departing from the scope of the claimed invention. Thus, the specific structural and functional details provided in the description are non-limiting, but serve merely as a basis for the invention defined by the claims provided herewith.

A novel cross-connector assembly 10 constructed in accordance with the present invention is illustrated in FIGS. 1-6. The cross-connector assembly 10 of the present invention is configured to fit to and securely connect two opposing bracing members or spinal rods, one at a first end 12 and the other at a second end 14 of the cross-connector assembly 10. The general configuration of a cross-connector assembly or transverse connector attached to a pair of spinal rods, which are in relative parallel-alignment with the spinal column of a subject is well illustrated by conventional devices such as shown in U.S. Pat. No. 6,554,832, issued to Shluzas U.S. Pat. No. 5,980,523, issued to Jackson, and U.S. Pat. No. 6,096,039 issued to Stoltenberg et al., the disclosures of which are each fully incorporated herein by reference. The cross-connector assembly 10 of the present invention similar to the devices disclosed in the immediately above incorporated references is configured for and capable of connection to a pair of spinal rods, which are secured in relative parallel alignment with the spinal column of a subject. However, due to the novel construction of the cross-connector assembly 10 of the present invention, the surgeon is now able to use a cross-connector that, as best shown in FIGS. 4A-4C can rotated about all three axes and translated about its longitudinal axis to shorten or length the device (FIG. 4D). The novel design of the present invention and its capability to be so easily configured and adjusted to securely fit the needs of individual subjects has never before been made available in the art of spinal surgery.

Figure 1:
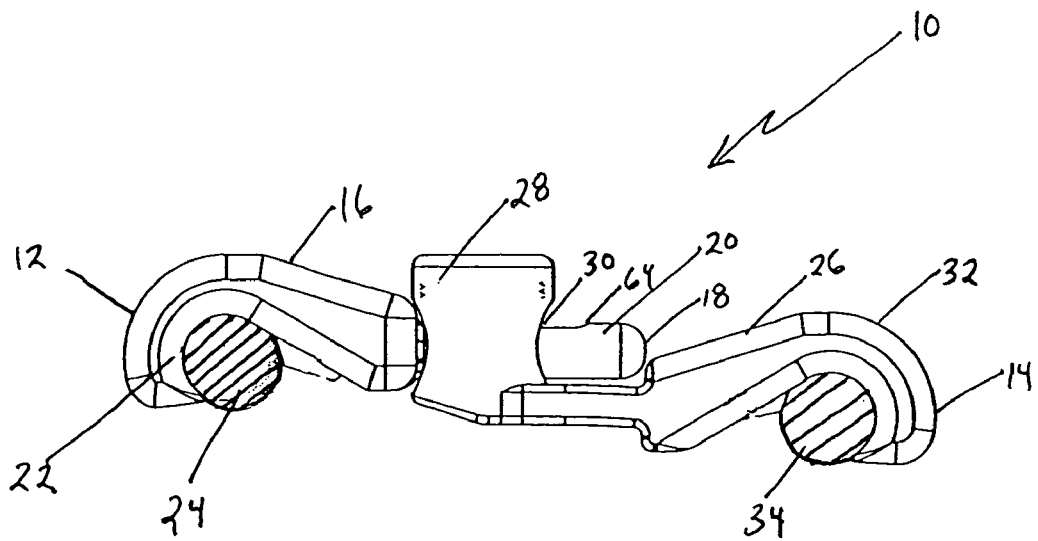
FIG. 1 shows a frontal view of the cross-connector assembly of the present invention with a representative spinal rod in a secured position in each of the spinal rod connector members.
Figure 2:
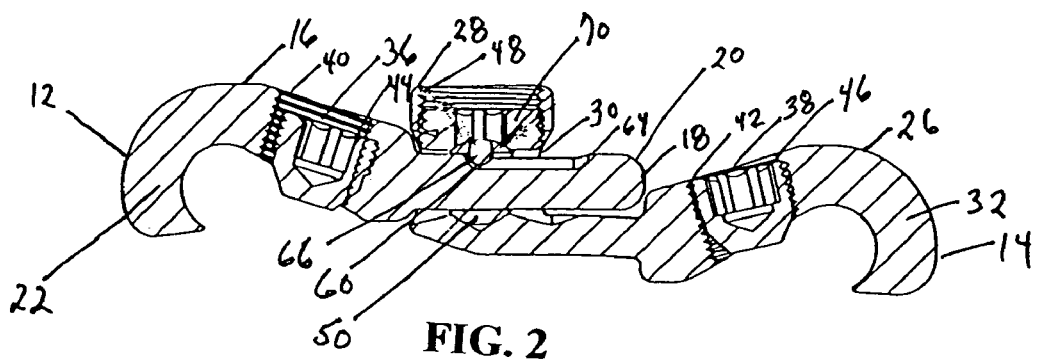
FIG. 2 shows a cross-sectional frontal view (Section A-A) of the cross-connector assembly shown in FIG. 1.
Figure 3:
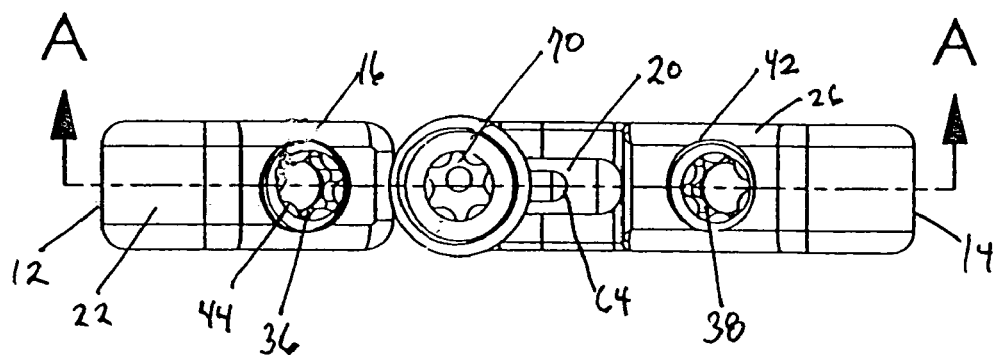
FIG. 3 shows a top view of the cross-connector assembly of the present invention and the section line (A-A) of the cross-sectional frontal view (Section A-A) of FIG. 2.

As best shown in FIGS. 1-3, the cross-connector assembly 10 is an elongated assembly having a first end 12 and a second end 14. A first connector, such as spinal rod connector 16 extends from the first end 12 of the cross-connector assembly 10 to a terminal end 18 of an arm, such as cylindrical arm 20. The first spinal rod connector 16, at the first end 12 of the cross-connector assembly 10 defines a first securing member, such as spinal rod clasping member 22. The first spinal rod clasping member 22 can have any shape that is suitable for attachment to a bracing member or rod but is preferably configured with a hook shaped design that is sized and configured to approximate the shape of the rounded contour of a first spinal rod, a representation of a transverse section of a first spinal rod is shown at 24.

A second connector, such as spinal rod connector 26, extends from the second end 14 of the cross connector assembly 10 toward the first end 12 of the cross-connector assembly 10 and terminates at an articulation assembly housing 28. The articulation assembly housing 28 defines an arm receiving portal 30, which is sized and configured to slidably and rotatably receive the arm 20 of the first spinal rod connector 16. The second spinal rod connector 26, at the second end 14 of the cross-connector assembly 10 defines a second spinal rod clasping member 32. The second spinal rod clasping member 32 can be configured with a hook shaped design that is sized and configured to approximate the shape of the rounded contour of a second spinal rod, a representation of a transverse section of a second spinal rod is shown at 34.

The first spinal rod 24 and the second spinal rod 34, when respectively positioned within the first clasping member 22 and the second clasping member 32, can be securely held in a releasably locked position by corresponding first and second clasping member set screws 36, 38. The first and second clasping member set screws 36, 38 are sized and configured to threadably attach to the respective first and second spinal clasping members 22 and 32 through respective first and second set screw receiving portals 40. 42, which are defined by the first and second clasping members 22, 32 respectively. The first and second set screw receiving portals 40, 42 are sized and configured to permit the respective first and second set screws 36, 38 to be threaded into and through the respective clasping members 22, 32 such that the set screws 36, 38 can make secure, locking contact with a respective first and a second spinal rod 24, 34, when such rods are properly positioned. The length of the first and second set screws 36, 38 can be such that when in the locked position and securely holding their respective spinal rods 24, 34 in place within the respective clasping member 22, 32, the respective heads 44, 46 of each of the first and second set screws 36, 38 will be approximately flush with or below the upper surface level of the respective first and second clasping members 22, 32. Thus, when a spinal rod 24, 34 is securely locked in place in the first and/or second clasping member 22, 32 the first and second set screws 36, 38 will not extend above the smooth contour of the upper surface of the first and second clasping members 22, 32 and therefore provide a low profile cross-connection assembly that is less obtrusive and irritating to adjacent tissue than is typical for many conventionally implanted devices.

Figure 5:
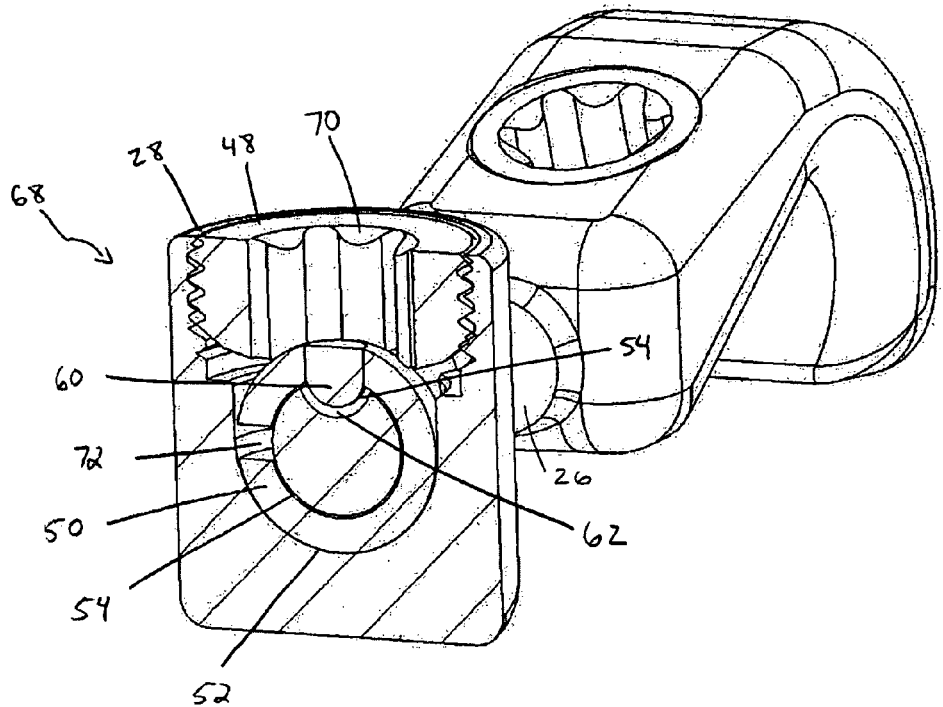
FIG. 5 shows a detail cross-sectional view of the joint assembly portion viewed along the transverse axis of the cross-connector assembly of the present invention.
Figure 6:
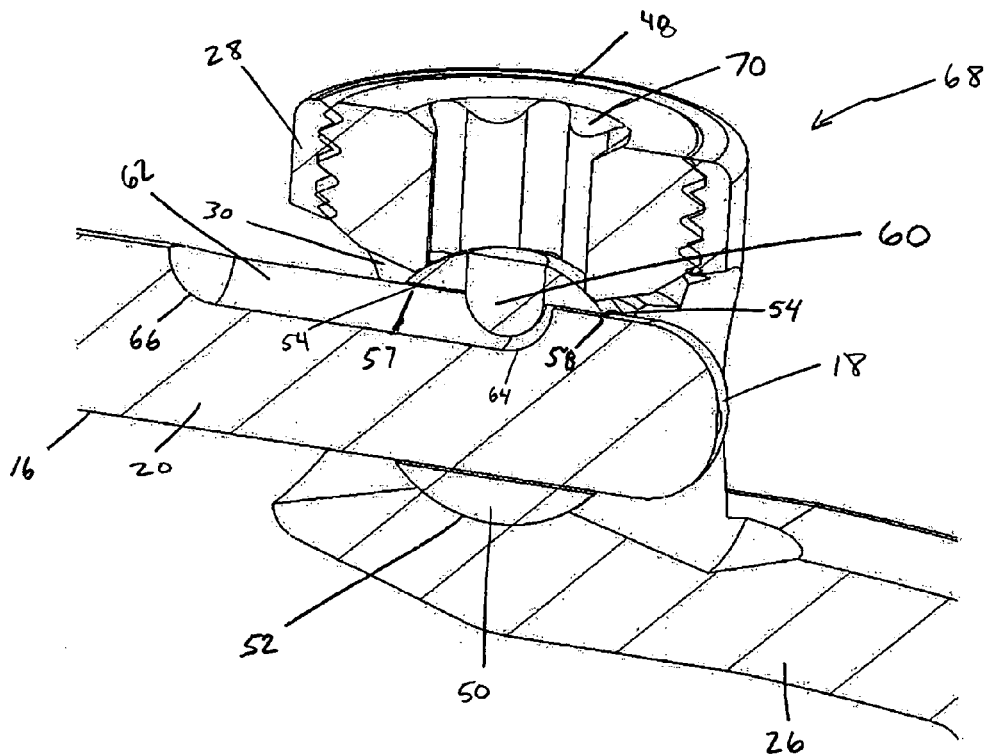
FIG. 6 shows a detail cross-sectional view of the joint assembly portion viewed along the longitudinal axis of the cross-connector assembly of the present invention.

The first spinal rod connector 16 and the second spinal rod connector 26 are adjustably connected one to the other by the passage of the cylindrical arm 20 of the first spinal rod connector 16 passing through the cylindrical arm receiving portal 30 of the articulation assembly housing 28 of the second connector 26. The articulation assembly housing 28 defines the cylindrical arm receiving portal 30 as a passage extending through the housing 28 along the longitudinal axis of the cross-connector assembly 10. The articulation assembly housing 28 also defines a threaded articulation assembly set screw portal 48, which extends downward toward the axis of the cylindrical arm receiving portal from the upper exterior of the articulation assembly housing 28 to a point extending below the cavity formed by the cylindrical arm receiving portal 30. Thus, the cylindrical arm receiving portal 30 and the articulation assembly set screw portal 48 jointly form a hollow interior space within the assembly housing 28, wherein the crossing of the respective axis of each of the two joining portals 30, 48 roughly resembles an inverted "T" shape. As best shown in FIGS. 2, 5, and 6, a novel split-ball articulation member 50 is sized and configured to be rotatably positioned within an articulation cavity 52, which is formed within the articulation housing 28 by the common space defined by the intersection cylindrical arm receiving portal 30 and the articulation assembly set screw portal 48.

As best shown in FIGS. 5 and 6, the size and configuration of the split ball articulation member 50 is such that the split ball defines a split ball interior passage 54 having a passage entrance 57 and passage exit 58 through which the cylindrical arm 20 can slidably pass along the longitudinal axis of the cross-connector assembly 10. As best shown in FIGS. 2, 5, and 6, the interior passage 52 of the split ball articulation member 50 includes a split ball guide pin 60 which protrudes into the interior passage 52 from the inner wall of the split ball interior passage 54. The split ball guide pin 60 is sized and configured to easily ride in a cylindrical arm guide pin slot 62, which is defined in the surface of the cylindrical arm 20.

Factors of growth, effects of age, injury, disease, and other influences can typically cause less than perfect symmetry in the spinal column of a subject. As a result, surgical devices and appliances such as the cross-connector assembly 10 of the present invention will be poorly fit to the spinal column of a subject unless the devices are capable of being easily and securely reconfigured for a more customized fit to the subject. The present invention provides a novel cross connector assembly that can be reconfigured by a surgeon to change the length of the assembly 10, the rotational alignment of the first and second ends 12, 14 to each other, the sideward alignment or azimuth relationship of the first and second ends 12, 14 to each other, and the elevation relationship of the first and second ends 12, 14 to each other. Each of these re-configurations, as shown in FIGS. 4A-4D, are made possible by the novel articulation assembly generally shown at 68 in FIGS. 5 and 6.

The articulation assembly 68, which includes the articulation assembly housing 28, the split ball articulation member 50, and the cylindrical arm 20 of the first spinal rod connector 16, makes it possible for a user to make each of the cross-connector assembly 10 re-configurations mentioned above.

Figure 4A:
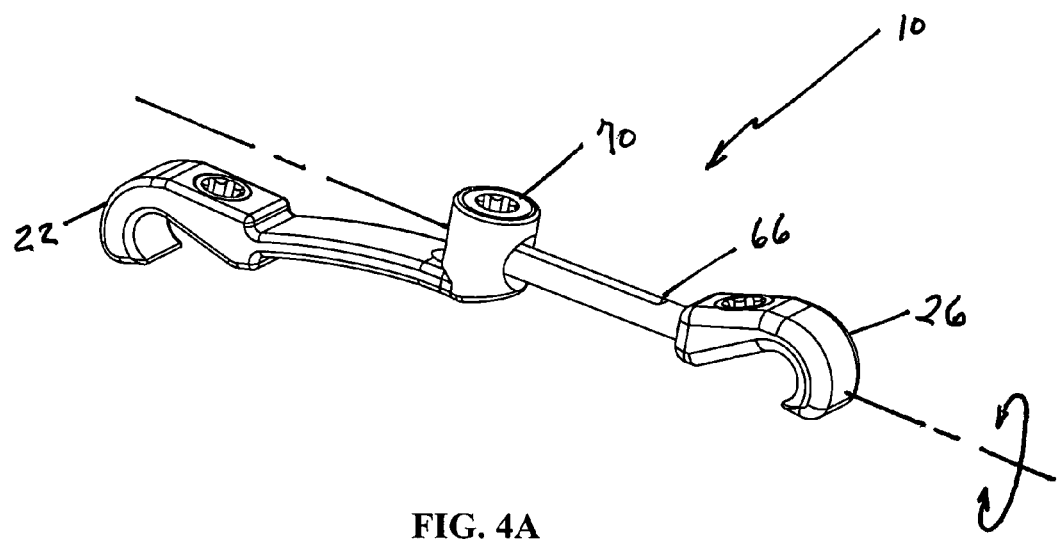
FIGS. 4A, 4B, 4C and 4D respectively show perspective views of the capacity to vary rotation in-part, vary azimuth, vary elevation, and vary length of the cross connector assembly of the present invention.
Figure 4B:
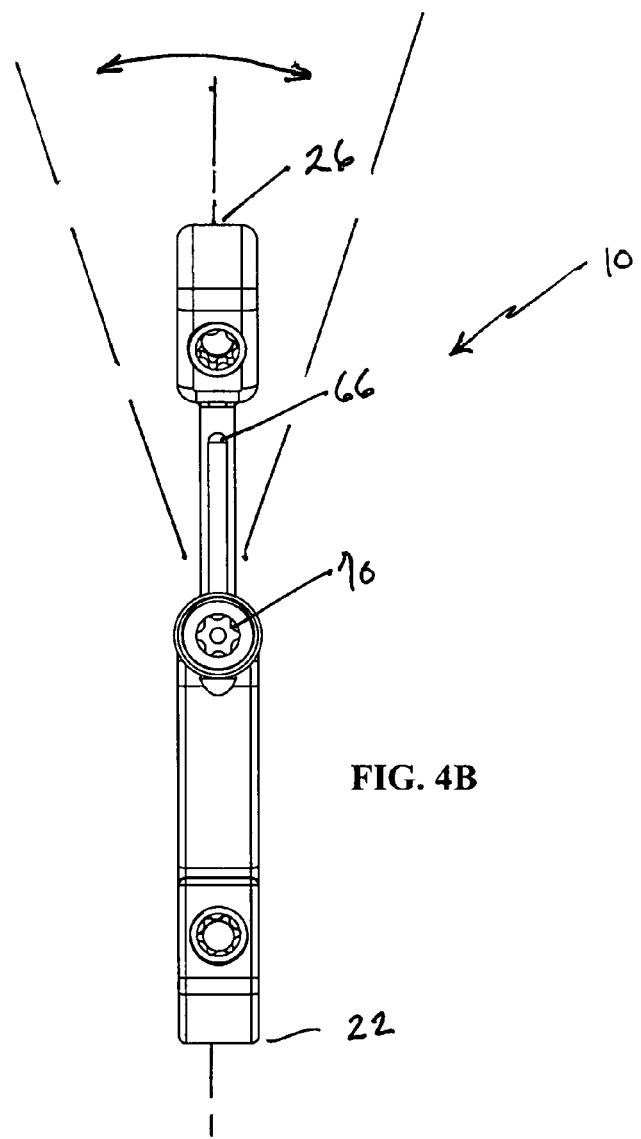
Figure 4C:
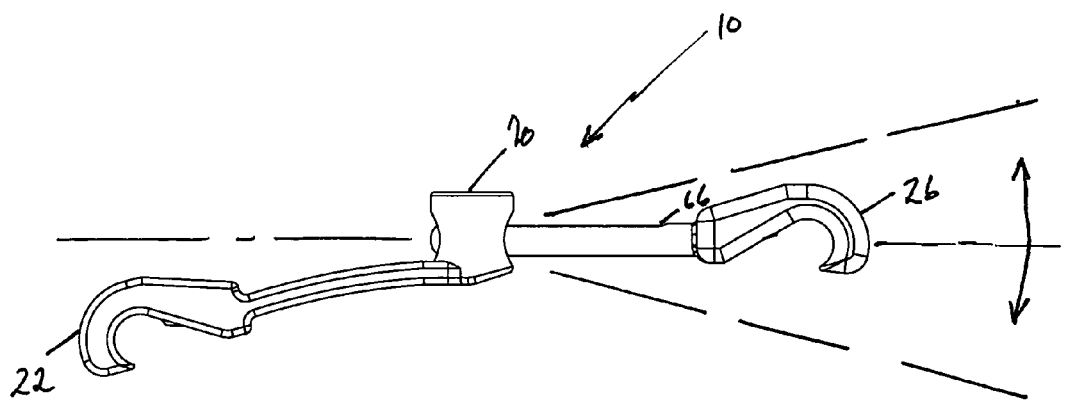
Figure 4D:
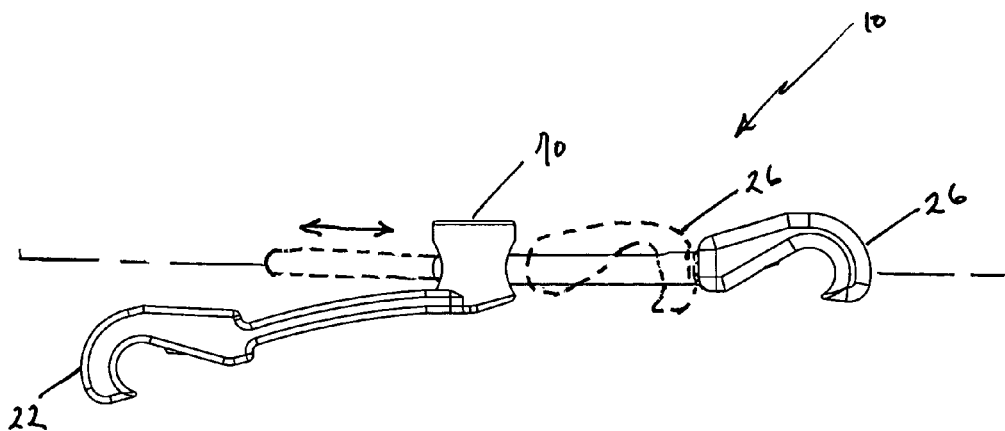

As shown in FIG. 4D, the length of the cross-connector assembly 10 can be adjusted by movement along the longitudinal axis of the assembly 10 of the first spinal rod connector 16 in relation to the second spinal rod connector 26. During such adjustment of the length of the cross-connector assembly 10, the split ball guide pin 60 of the split ball articulation member 50 is held in position by the articulation assembly housing 28 while the first spinal rod connector 16 with its cylindrical arm 20 and integral cylindrical arm guide pin slot 62 are adjusted inwardly or outwardly along the longitudinal axis of the cross-connector assembly 10. When such relative movement of the first and second spinal rod connectors 16, 26 is made, the interaction of the guide pin 60 as it slides along the length of the guide pin slot 62 serves to control the extent of such movement. As best shown in FIGS. 2 and 6, the cylindrical arm guide pin slot 62 has a distal stop 64 and a proximal stop 66 (FIGS. 2, 4A-B, and 6), which serve the purpose of limiting the movement of the guide pin 60 only to positions in the guide pin slot 62 that are between the distal and proximal stops 64, 66.

The split ball articulation member 50 can be rotated within the articulation assembly housing 28 so as to change the rotational relationship of the first and second spinal rod connectors 16, 26 in relation to each other. Such rotation of the split ball articulation member 50 allows the user to simultaneously reconfigure the cross-connector assembly 10 in more than one plane or dimension, such that the rotational alignment (FIG. 4A), the azimuth alignment (FIG. 4B), and the elevation alignment (FIG. 4C) of the cross-connector assembly 10 can be quickly and easily adjusted.

The cross-connector assembly 10, after being reconfigured by the user to provide a best fit to the subject to which the device is to be applied, can be quickly and securely but releasably locked into the selected configuration. As shown in FIGS. 2, 3, 4A-4B, 5, and 6, an articulation set screw 70 is configured to threadably engage the articulation assembly set screw portal 48 so as to bring pressure against the split ball articulation member 50 when screwed into the articulation assembly housing 28 in a locked position. When in a locked position, as best shown in FIGS. 5 and 6, the articulation set screw 70 contacts the split ball articulation member 50 at whatever rotational position it may be in and holds it fast within the articulation cavity 52. By locking the split ball 50 into a specific position within the articulation cavity 52, further movement of cross-assembly connector components to alter the configuration of rotation, azimuth, or elevation are made impossible. A split ball slit 72 is defined by and along a portion of the circumference of the split ball articulation member 50. The split ball slit 72 is of a size, depth, and length along a portion of the circumference of the split ball articulation member 50 to as to allow flexible and reversible deformation and compression inward of the split ball articulation member 50 when sufficient force is applied by the inward movement of the articulation set screw 70 against the split ball articulation member 50. Upon compression of the split ball actuation member 50 by the articulation set screw, the split ball slit 72 narrows and allows the adjacent portions of the split ball articulation member to make locking contact against the surface of the cylindrical arm 20. Such locking contact serves to stop further slidable movement of the cylindrical arm 20 through the split ball interior passage 54 and the cylindrical arm receiving portal 30.

Locking of the articulation assembly 68 so as to stop unwanted further reconfiguration of the cross-connector assembly 10 can be done simultaneously for all axis of movement of the assembly by forcefully and fully tightening the articulation set screw 70 into a locked position within the articulation assembly housing. Alternatively, by threadably adjusting the articulation set screw 70 into the articulation assembly set screw portal 48 only to a position that results in locking contact with the split ball 50 and stops further rotation of the split ball 50 within the articulation cavity 52 can still allow slidable movement of the cylindrical arm 20 through the split ball interior passage 54. In this alternative two-step locking process, after the length of the cross-connector 10 is adjusted by movement of the cylindrical arm 20, an additional application of force by the articulation set screw 70 can result in compression of the split ball 50 to stop further movement of the cylindrical arm 20.

It is within the concept of the present invention that the articulation assembly 68 can be configured such that the mechanism permits the location of the articulation set screw 70 to be in alignment with the transverse axis of the connector assembly 10, that is to be located on the side of the articulation assembly housing 28.

Thus, the present invention provides a novel cross-connector assembly that can be simultaneously, securely, and releasably reconfigured to adjust the length, azimuth, elevation, and rotation of the components of the device relative to each other.

The materials used to construct the present invention are those which have sufficient strength, resiliency, and biocompatability as is well known in the art for such devices. Methods of manufacture of such surgical implant devices is also well known in the art.

It is within the concept of the present invention to provide the cross-connector assembly 10 as part of a kit for use in a surgical process, the kit comprising at least the cross-connector assembly and at least some of the associated tools for using said cross-connector assembly. In addition, the kit can contain spinal rods and associated screws or connectors for connecting the rods to the bone of a subject.

Each of the embodiments described above are provided for illustrative purposes only and it is within the concept of the present invention to include modifications and varying configurations without departing from the scope of the invention that is limited only by the claims included herewith.

What is claimed is:

1. A novel cross-connector assembly for securing two bracing members one to the other, the cross-connector assembly comprising:
    an elongated first connector having a first connector longitudinal axis, configured at a first end of said cross-connector assembly to attach to a first bracing member and configured at a second end to have a cylindrical arm;
    an elongated second connector having a second connector longitudinal axis, configured at a second end of said cross-connector assembly to attach to a second bracing member and configured at a first end to form an articulation assembly housing;
    an articulation assembly positioned between said first end and said second end of said cross-connector assembly and movably connecting said first connector to said second connector, said articulation assembly comprising said articulation assembly housing and a split ball articulation member rotatably contained within an articulation cavity of said housing, said split ball articulation member defining a split ball interior passage sized and configured to slidably receive said cylindrical arm of said first connector, said split ball interior passage being partially obstructed by a cylindrical arm guide pin protruding from said split ball articulation member into said split ball interior passage and said cylindrical arm defining along at least one surface a cylindrical arm guide pin slot, said cylindrical arm guide pin being sized and configured to slidably pass within said cylindrical arm guide pin slot when said cylindrical arm moves in relation to said split ball articulation member, said articulation assembly housing having an arm receiving portal, whereby said arm receiving portal is defined as extending entirely through said articulation assembly housing in parallel alignment with said first connector longitudinal axis of said cross-connector assembly such that said cylindrical arm of said first connector extends into said housing to contact and slidably pass through said split ball interior passage, said articulation assembly housing defining an articulation assembly set screw portal extending through said articulation assembly housing and making a common spatial connection to said arm receiving portal, said common spatial connection being the articulation cavity for said split ball articulation member, the articulation assembly further comprising an articulation set screw sized and configured to threadably engage the articulation assembly set screw portal;
    wherein rotation of said split ball articulation member within said housing and slidable movement of said cylindrical arm can effect rotational movement of said first connector relative to said second connector around all three axes of said device and translation movement to shorten or lengthen the device along its longitudinal axis, said movement around said three axes being directional adjustments of said first connector longitudinal axis relative to said second connector longitudinal axis so as to alter relative rotation, azimuth, and elevation of said second connector to said first connector.

2. The assembly according to claim 1, wherein said articulation assembly set screw is configured, when fully inserted into the articulation assembly set screw portal, to make locking contact with said articulation member such that said articulation member is securely held between said articulation set screw and at least one interior wall of said articulation cavity.

3. The assembly according to claim 1, wherein said split ball articulation member comprises a split ball slit defined in a portion of a circumference of said split ball articulation member such that upon compressing contact by said articulation set screw against said split ball articulation member, said split ball slit narrows sufficiently to allow said split ball articulation member to compress into a locking relationship with said cylindrical arm of said first connector.

4. The assembly according to claim 3, wherein said assembly is configured such that said articulation set screw can be threadably moved into contact with said split ball articulation member only to a degree so as to stop rotation of said split ball articulation member while still permitting sliding motion of said cylindrical arm within said articulation member; thereby providing a partial lock of said assembly.

5. The assembly according to claim 1, wherein said first connector defines a first set screw portal and said second connector defines a second set screw portal.

6. The assembly according to claim 5, further comprising a first set screw sized and configured to be threadably engaged with said first set screw portal and a second set screw sized and configured to be threadably engaged with said second set screw portal, both first set screw and second set screw being configured to be flush with or below an upper surface of said cross-connector assembly when said set screws are in an inserted and locked position, said locked position being such that the assembly is releasably locked to a first and second opposing bracing member.

7. The assembly according to claim 6, wherein said first and second bracing members are spinal rods.

8. A method of connecting two bracing members one to the other, the method comprising:
    providing the cross-connector assembly of claim 6;
    clasping and securing a first bracing member in said first connector;
    adjusting position of said second connector in spatial relationship to said first connector so as to bring a said second connector into a properly aligned clasping relationship with a second bracing member;
    inserting and locking all set screws into said cross-connector assembly to securely clasp said first bracing member and said second bracing member and to secure said cross-connector assembly in said adjusted position.

9. A kit for use in a surgical procedure to fuse at least two adjacent vertebra, one to the other, the kit comprising: at least one device according to claim 1, associated tools for said device, and a sterile package for said kit.

10. The kit according to claim 9, wherein said at least one device is a plurality of said devices.

* * * * *